(12) United States Patent
Shin et al.

(10) Patent No.: US 11,998,174 B2
(45) Date of Patent: Jun. 4, 2024

(54) ENDOSCOPE HAVING CHAIN LOCKING PREVENTION FUNCTION

(71) Applicant: TAEWOONG MEDICAL CO., LTD., Gimpo-si (KR)

(72) Inventors: Kyong Min Shin, Gyeonggi-do (KR); Sung Hwan Park, Gimpo-si (KR); Hyun Soo Ji, Gimpo-si (KR)

(73) Assignee: TAEWOONG MEDICAL CO., LTD., Gimpo-si (KR)

( * ) Notice: Subject to any disclaimer, the term of this patent is extended or adjusted under 35 U.S.C. 154(b) by 170 days.

(21) Appl. No.: 17/014,340

(22) Filed: Sep. 8, 2020

(65) Prior Publication Data

US 2021/0068619 A1 Mar. 11, 2021

(30) Foreign Application Priority Data

Sep. 11, 2019 (KR) .......................... 10-2019-0112949

(51) Int. Cl.
*A61B 1/005* (2006.01)
*A61B 1/00* (2006.01)
*A61B 1/06* (2006.01)

(52) U.S. Cl.
CPC ........ *A61B 1/0051* (2013.01); *A61B 1/00002* (2013.01); *A61B 1/00066* (2013.01); *A61B 1/00071* (2013.01); *A61B 1/00112* (2013.01); *A61B 1/0669* (2013.01); *A61B 2560/04* (2013.01)

(58) Field of Classification Search
CPC ......... A61B 34/30; A61B 34/70; A61B 34/71; A61B 1/0669; A61B 1/0051; A61B 1/00066; A61B 1/0655; A61B 1/0052; A61B 1/0057; A61B 1/008; A61B 1/00112; A61B 1/01; A61B 1/053; A61B 1/00002; A61B 1/00071; A61B 2017/00318
USPC ....................................................... 600/149
See application file for complete search history.

(56) References Cited

U.S. PATENT DOCUMENTS

| 5,320,021 | A  | * | 6/1994 | Heintz ................... B25B 13/52 |
| | | | | 81/3.43 |
| 9,392,932 | B2 | * | 7/2016 | Ishizaki .............. G02B 23/2476 |
| 2017/0007106 | A1 | * | 1/2017 | Koyama .............. A61B 1/0051 |
| 2019/0246877 | A1 | * | 8/2019 | Mitsuya ............. A61B 1/00066 |

FOREIGN PATENT DOCUMENTS

| KR | 10-0673412 B1 | 1/2007 |
| KR | 10-1091999 B1 | 12/2011 |
| KR | 10-1783225 B1 | 9/2017 |

* cited by examiner

*Primary Examiner* — Michael J Carey
*Assistant Examiner* — Megan Elizabeth Monahan
(74) *Attorney, Agent, or Firm* — Bridgeway IP Law Group, PLLC; Jihun Kim

(57) ABSTRACT

An endoscope includes: a direction conversion module for converting rotational motions of the upper and lower sprockets to linear motions of the upper and lower chains while maintaining linear states of the upper and lower chains pulled, and pushed upon rotational operation of the operation part, in which the direction conversion module includes: first and second connection blocks for connecting both ends of the upper chain to one end of each of the first and second connection wires of the operation part, and third and fourth connection blocks for connecting both ends of the lower chain to one end of each of the third and fourth connection wires of the operation part.

3 Claims, 8 Drawing Sheets

ENDOSCOPE HAVING CHAIN LOCKING PREVENTION FUNCTION

TECHNICAL FIELD

The present disclosure relates to an endoscope, and more specifically, to an endoscope having a chain locking prevention function, which may linearly and stably maintain a parallel state of a chain, which has the middle portion of the length wound around a sprocket and both ends reciprocating in opposite directions, at all times upon rotational operation of an operation part for operating the front end of an insertion part to be bent vertically and horizontally, thereby preventing locking and performing the rotational operation precisely and smoothly.

BACKGROUND ART

Generally, in a surgery using an endoscope, a camera-installed endoscope and a surgical tool are inserted through a small hole without largely incising a human body, and then the surgery is conducted while examining a patient's affected area through the image photographed by the endoscope in a body.

Particularly, the endoscopic surgery starting from laparoscopic surgery has an advantage in that the scar area is small and the bleeding is also less because an incision site is small compared to laparotomy, so that a recovery time of the patient is short after the surgery.

Recently, not only the technology has been developed to enable the endoscopic surgery for almost all surgeries requiring laparotomy, but also the endoscopic surgery is increasingly applied in other medical fields.

A conventional general endoscope is integrally composed of an insertion part inserted into the human body and an operation part for controlling the insertion part, and a plurality of pipelines and guides are embedded therein through the inside of each part, and particularly, since an imaging element such as an expensive CCD or the like is provided on the front end of the insertion part inserted into the body, there is a problem in that it is difficult to separate only the insertion part from the operation part to be replaced with new one.

(Patent Document 1) KR10-0673412B1
(Patent Document 2) KR10-1091999B1
(Patent Document 3) KR10-1783225B1

Patent Documents 1 to 3 disclose various types of endoscopes which may couple and use the insertion part inserted into the body and the operation part for operating the insertion part or separate and store the insertion part and the operation part according to the trend of further strengthening the hygiene function of the endoscope used for medical use in recent years.

In order to operate the front end of the insertion part to be bent vertically and horizontally in the endoscopes disclosed in these Patent Documents, a pair of wires having one end connected to the inside of the front end of the insertion part linearly reciprocate using the external force transferred through both ends of the chain by converting the direction into the linear direction through the chain wound around the sprocket performing the rotational motion by the rotational operation of an operation handle.

It is possible to operate to vertically or horizontally bend the front end of the insertion part by pulling or pushing the pair of wires.

Meanwhile, as illustrated in FIG. 8, both ends of a chain 26 wound around a sprocket 25 of rotational operation handles 29*a*, 29*b* provided in an operation part 20 coupled to an insertion part 10 are connected to different wires 11, 22 of the insertion part via the pair of wires 21, 22, respectively and disposed parallel to each other, so that the pulling movement and the pushing movement of the chain 26 parallel to each other are simultaneously performed in opposite directions.

However, if the speeds and distances of the chain pulled, and pushed in the opposite directions in a direction conversion section which converts the rotational motion of the sprocket 25 into the linear motion of the chain 26 are inconsistent with each other, the chain 26 has a plurality of link members linked and connected to each other via pin members, so that the link connection portions between the link members are not arranged linearly and a bending portion bent inward or outward is generated.

There occurs a fatal problem of losing the endoscopic function in that the bending portion of the chain generates a noise due to the interference with other adjacent members in the process of passing through the internal passage of the narrow direction conversion section of the operation part, and it is difficult to precisely perform the endoscopic surgery due to the difficulty in the precise control of the pulling movement amount or the pushing movement amount of the chain caused by the rotational amount of the rotational operation handle by the bending portion, whereas the function of the endoscope is lost due to the operation failure caused by the narrowness if the bending portion is formed to be larger than necessary.

DISCLOSURE

Technical Problem

Therefore, the present disclosure is intended to solve the above problems, and an object of the present disclosure is to provide an endoscope having a chain locking prevention function, which artificially gives an external force such as an elastic support force to a chain which linearly reciprocates in opposite directions upon rotational operation of an operation part, thereby stably maintaining the linear state at all times so as to prevent the bending or locking of a chain in the process in which the middle portion of the length of the chain is wound around a sprocket and both ends thereof are arranged parallel to each other and reciprocate.

The object to be achieved in the present disclosure is not limited to the aforementioned object, and other objects not mentioned will be clearly understood to those skilled in the art to which the present disclosure pertains from the following description.

Technical Solution

As a specific means for achieving the object, a preferred exemplary embodiment of the present disclosure provides an endoscope having a chain locking prevention function including an insertion part having a lighting photographing part on a front end thereof, and an operation part having upper and lower chains having the middle portions of the lengths wound around upper and lower sprockets of a rotary shaft and operating the front end of the insertion part to be bent, a direction conversion module for converting rotational motions of the upper and lower sprockets to linear motions of the upper and lower chains while maintaining linear states of the upper and lower chains pulled, and pushed upon rotational operation of the operation part, in which the direction conversion module includes: first and second connection blocks for connecting both ends of the upper chain to one end of each of the first and second connection wires of the operation part, and third and fourth connection blocks for connecting both ends of the lower chain to one end of each of the third and fourth connection wires of the operation part, includes: a first guide rail having a predetermined length disposed between the first connection block and the third connection block to guide the slide movements of the first and third connection blocks, and a second guide rail having a predetermined length disposed between the second connection block and the fourth connection block to guide the slide movements of the second and fourth connection blocks, and includes: first and second coil springs having both ends connected between one end of each of the first and second guide rails and the first and second connection blocks and elastically supporting the first and second connection blocks connected to the first and second connection wires toward the insertion part, and third and fourth coil springs having both ends connected between one end of each of the first and second guide rails and the third and fourth connection blocks and elastically supporting the third and fourth connection blocks connected to the third and fourth connection wires toward the insertion part.

At this time, the first, second, third, and fourth connection blocks may include: locking grooves recessed so as to be locked and connected to a locking member provided on one end of each of the first, second, third, and fourth connection wires.

At this time, the direction conversion module includes: an intermediate guide plate having both ends contacting between the first guide rail and the second guide rail, an upper guide plate assembled on one side surface of the intermediate guide plate contacting one side surface of each of the first and second connection blocks and located between the upper chain parallel to each other, and a lower guide plate assembled on the other side surface of the intermediate guide plate contacting one side surface of each of the third and fourth connection blocks and located between the lower chain parallel to each other.

At this time, the direction conversion module includes: an upper finishing plate assembled with the upper guide plate so that one side surfaces of the first and second connection blocks contact an inner surface thereof while covering a connection portion between the first and second connection blocks and the first and second connection wires, and a lower finishing plate assembled with the lower guide plate so that one side surfaces of the third and fourth connection blocks contact an inner surface thereof while covering a connection portion between the third and fourth connection blocks and the third and fourth connection wires.

At this time, the first and second coil springs may be stretched to both sides at the same lengths and connected in a state of generating elastic restoring forces, so as to transfer external forces having the same strengths to both ends of the upper chain through the first and second connection blocks, or the third and fourth coil springs may be stretched to both sides at the same lengths and connected in a state of generating elastic restoring forces, so as to transfer external forces having the same strengths to both ends of the lower chain through the third and fourth connection blocks.

At this time, both ends of each of the upper and lower chains may be coupled to one end of each of the first, second, third, and fourth connection blocks via a chain coupling part, and the chain coupling part may include: coupling male screws provided on both ends of each of the upper and lower chains to be rotationally operated, and coupling female screw holes formed on one ends of the first and second connection blocks so as to be screw-coupled to the coupling male screw.

Advantageous Effects

The preferred exemplary embodiment of the present disclosure described above has the following effects.

By providing the first, second, third, and fourth coil springs for elastically supporting both ends of the upper and lower chains having the middle portions of the lengths wound around the upper and lower sprockets toward the insertion part, it is possible to maintain the upper and lower chains, which are linearly pulled, and pushed by the selective rotation of the operation part, in the linear state, thereby fundamentally preventing the occurrence of noise and the narrowness accident due to the contact between the bending portion generated in the middle portion of the length of the chain having the plurality of link members linked and connected by the pin members and other members, whereas it is possible to precisely control the pulling and pushing movements of the upper and lower chains wound around the upper and lower sprockets, thereby precisely and stably performing the endoscopic surgery and increasing reliability for the medical equipment.

BEST MODE

Figure 1:
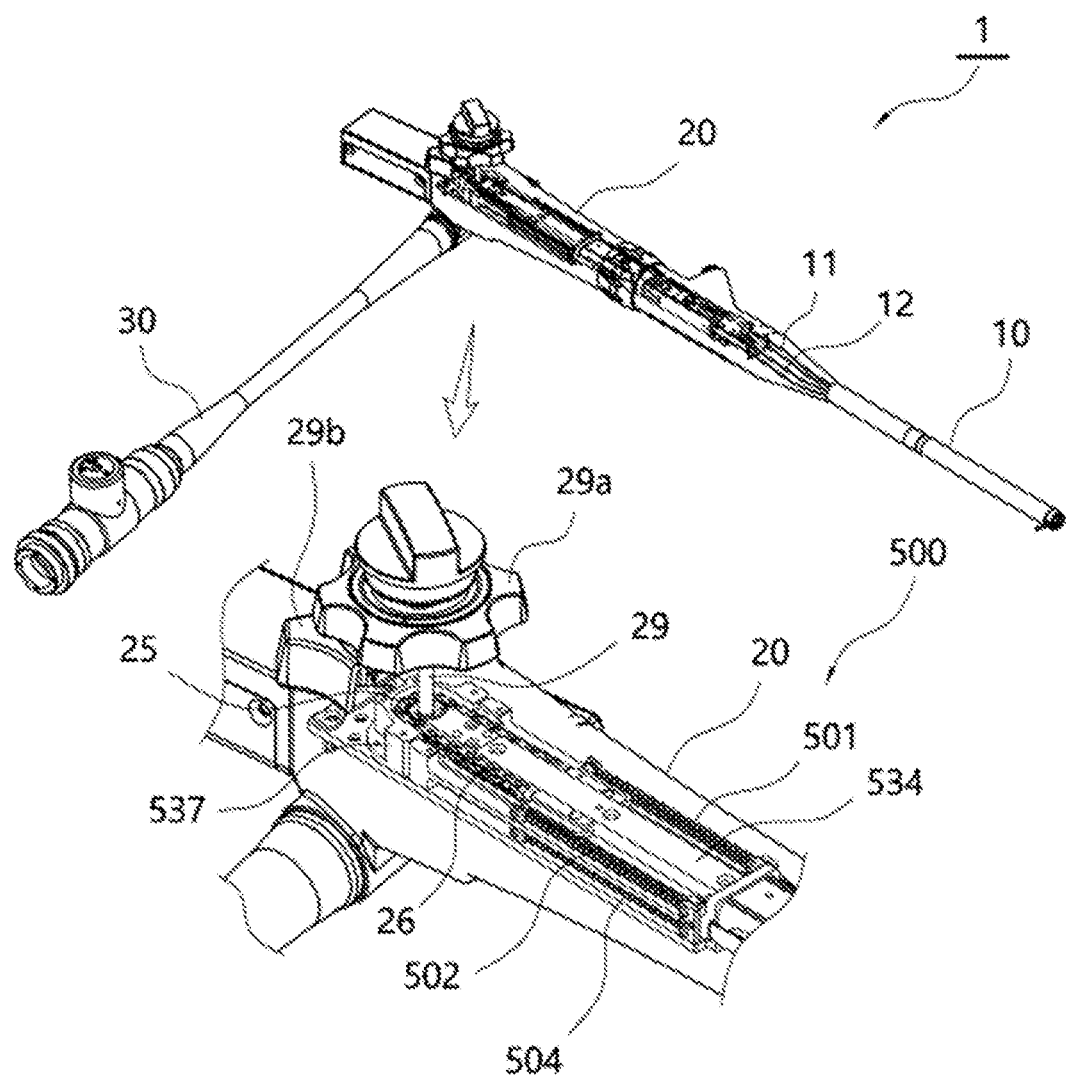
FIG. 1 is a perspective diagram illustrating an overall endoscope having a chain locking prevention function according to an exemplary embodiment of the present disclosure.

Hereinafter, preferred exemplary embodiments of the present disclosure will be described in detail with reference to the accompanying drawings so that those skilled in the art to which the present disclosure pertains may easily practice the present disclosure. However, in specifically describing a structural principle of the preferred exemplary embodiments of the present disclosure, detailed descriptions of the related and known functions or components will be omitted if it is determined that the detailed descriptions thereof may unnecessarily obscure the gist of the present disclosure.

In addition, the same reference numerals are used for the parts having similar functions and operations throughout the drawings.

In addition, throughout the specification, when a part is said to be 'connected' to another part, the part is not only 'directly connected' to another part, but also 'indirectly connected' to another part with other elements interposed therebetween. In addition, the term 'including' a component means that other components may be further included, rather than excluding other components, unless specially stated otherwise.

As illustrated in FIG. 1, an endoscope 1 according to an exemplary embodiment of the present disclosure includes an insertion part 10 having a front end inserted into a body upon endoscopic surgery, an operation part 20 having a plurality of operation handles, an universal joint 30 electrically connected to an endoscope control management system, and a detachable unit for coupling the insertion part 10 to the operation part 20 to mechanically connect them before the endoscopic surgery or separating the insertion part 10 and the operation part 20 after the endoscopic surgery.

The insertion part 10 is made of a flexible tube material to adjust a direction of being inserted into a body, and has a lighting photographing part having a light source illuminating the in-body and an image sensor for photographing the in-body on the front end thereof.

The operation part 20 includes an upper operation handle 29a for operating the front end of the insertion part inserted into the body to be vertically bent and a lower operation handle 29b for operating the front end of the insertion part to be horizontally bent.

Upper and lower sprockets 25, 27 provided on the upper and lower operation handles, respectively and upper and lower chains 26, 28 connected to the upper and lower sprockets 25, 27, respectively are provided inside the operation part 20, thereby converting selective rotational motions of the upper and lower operation handles into linear motions, and both ends of each of the upper and lower chains 26, 28 are disposed inside the insertion part via a plurality of connection wires disposed inside the operation part and connected to the other end of each of a plurality of operation wires having one ends connected to the inside of the front end of the insertion part.

By converting the rotational motion into the linear motion which pulls and moves, and pushes and moves a pair of operation wires among the plurality of operation wires disposed within the insertion part through the upper and lower chains having the middle portions of the lengths wound around the upper and lower sprockets rotated by the selective rotations of the upper and lower operation handles by the user, the front end of the insertion part is bent in the body vertically or horizontally according to the linear motion of the operation wire.

The operation part is provided with an operation switch and an operation button for putting or discharging liquid and gas for cleaning and disinfection upon endoscopic surgery, and the rear end of the insertion part detachably assembled with the front end of the operation part via the detachable unit is provided with a doorway through which a surgical element, such as an endoscopic treatment tool having a clip, enters into and exits from the insertion part and a cap for opening and closing the doorway.

Figure 2:
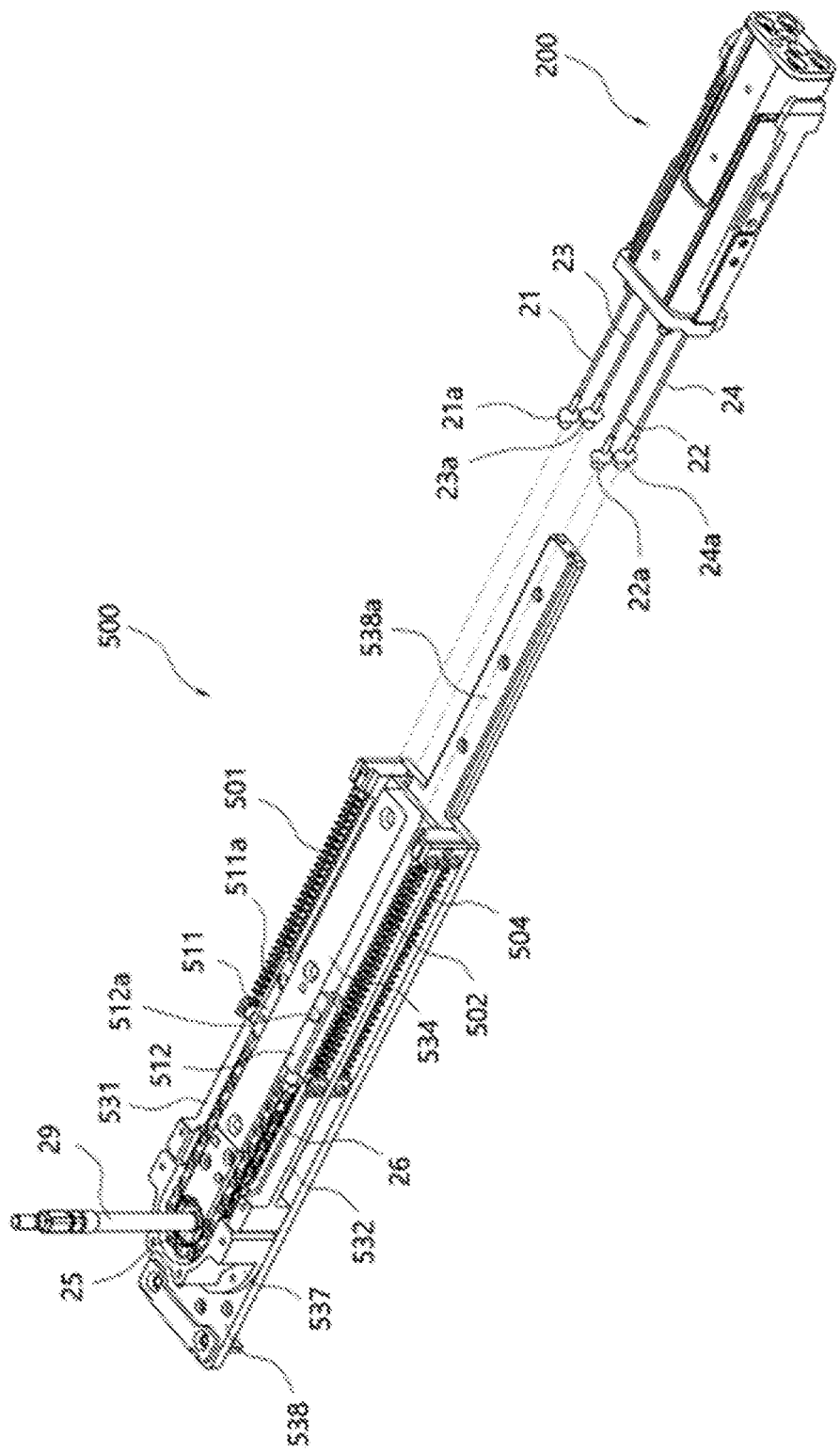
FIG. 2 is a perspective diagram illustrating a direction conversion module and a second detachable module provided in an operation part of the endoscope having the chain locking prevention function according to the exemplary embodiment of the present disclosure.

As illustrated in FIGS. 1 and 2, the endoscope 1 having the chain locking prevention function according to the preferred exemplary embodiment of the present disclosure includes a direction conversion module 500 for converting the rotational motions of the upper and lower sprockets 25, 27 to the linear motions of the upper and lower chains while maintaining the linear states of the upper and lower chains 26, 28 pulled, and pushed upon the selective rotational operation of the operation part.

Although it has been illustrated and described that the direction conversion module 500 is adopted to the operation part 20 of the detachable endoscope including the detachable unit which detachably couples between the rear end of the insertion part 10 and the front end of the operation part 20, the direction conversion module is not limited thereto, and may be operated by being also applied to an integral endoscope, in which the insertion part and the operation part are integrally connected to each other, and one wire with the connection wire and the operation wire connected to each other is provided, in the same manner.

The detachable unit includes a first detachable module disposed inside the insertion part, and a second detachable module disposed inside the operation part to connect the operation wire of the first detachable module to the connection wire of the second detachable module upon correspondingly coupling the insertion part and the operation part separated from each other.

The first detachable module includes first and second operation wires disposed parallel to each other inside the insertion part and moved in opposite directions so as to operate the front end of the insertion part to be vertically bent, and third and fourth operation wires disposed parallel to the first and second operation wires and moved in opposite directions so as to operate the front end of the insertion part to be horizontally bent.

The second detachable module 200 includes first and second connection wires 21, 22 connected to both ends of the upper chain wound around the upper sprocket and parallel to each other, and third and fourth connection wires 23, 24 connected to both ends of the lower chain wound around the lower sprocket and parallel to each other.

Here, although it has been illustrated and described that the first and second connection wires 21, 22 operate the front end of the insertion part to be vertically bent in conjunction with a pair of the first and second operation wires 11, 12 disposed parallel to each other on the upper side inside the insertion part in the figure, whereas the third and fourth connection wires 23, 24 operate the front end of the insertion part to be horizontally bent in conjunction with a pair of the third and fourth operation wires 13, 14 disposed parallel to each other on the lower side inside the insertion part in the figure, the present disclosure is not limited thereto and the vertically and horizontally bending operations may be performed conversely according to an endoscope design.

In addition, although it has been illustrated and described that the rotations of the upper and lower sprockets are performed by the manual rotational operation of the worker gripping the upper and lower operation handles provided in the operation part, the rotations of the upper and lower sprockets are not limited thereto and may be performed by connecting a rotary shaft assembled with the upper and lower sprockets to a driving means such as a motor and using a separate remote operation means such as a joystick for controlling the driving means.

Figure 3:
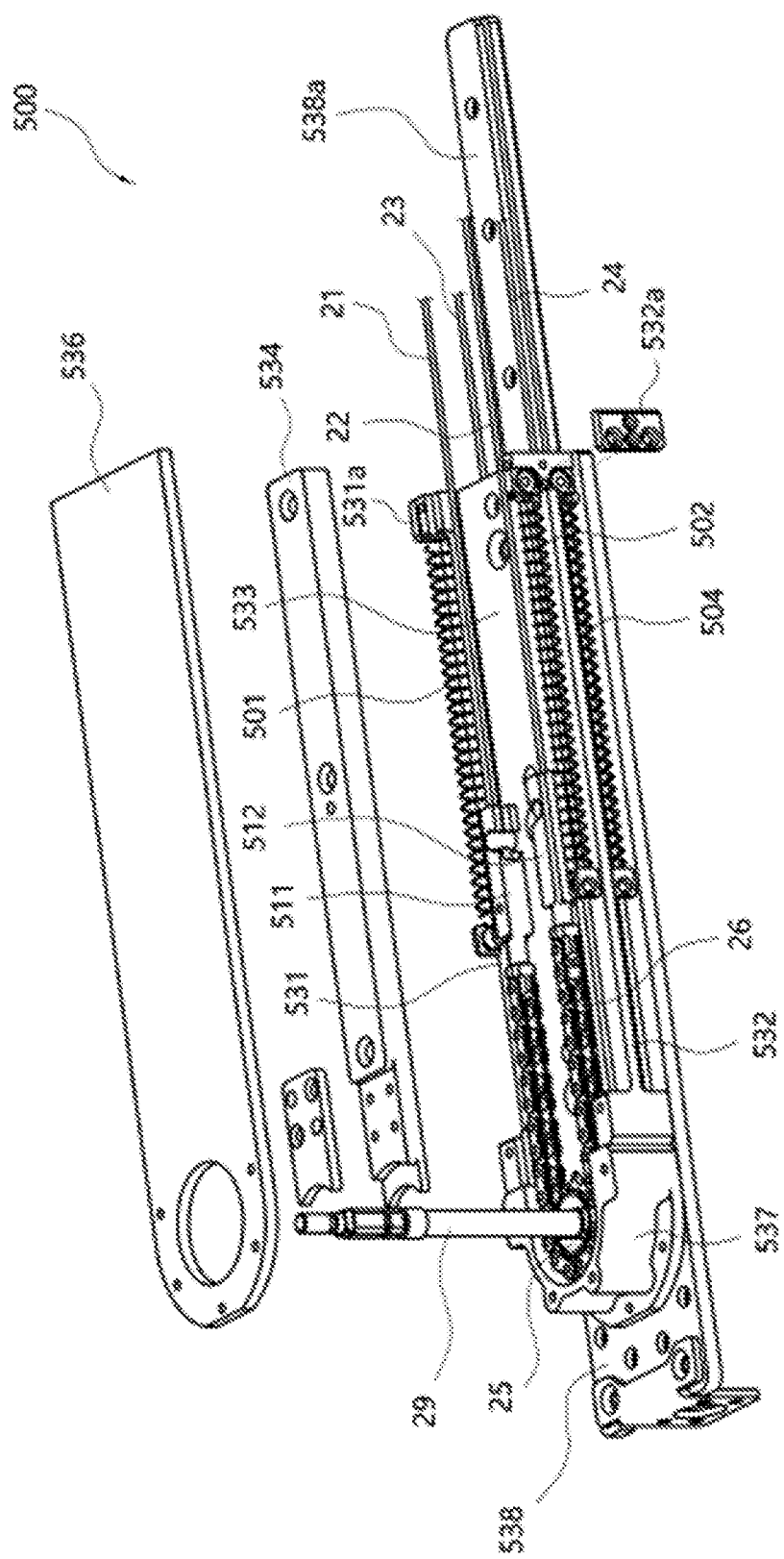
FIG. 3 is a perspective diagram illustrating an overall direction conversion module provided in the endoscope having the chain locking prevention function according to the exemplary embodiment of the present disclosure.
Figure 4:
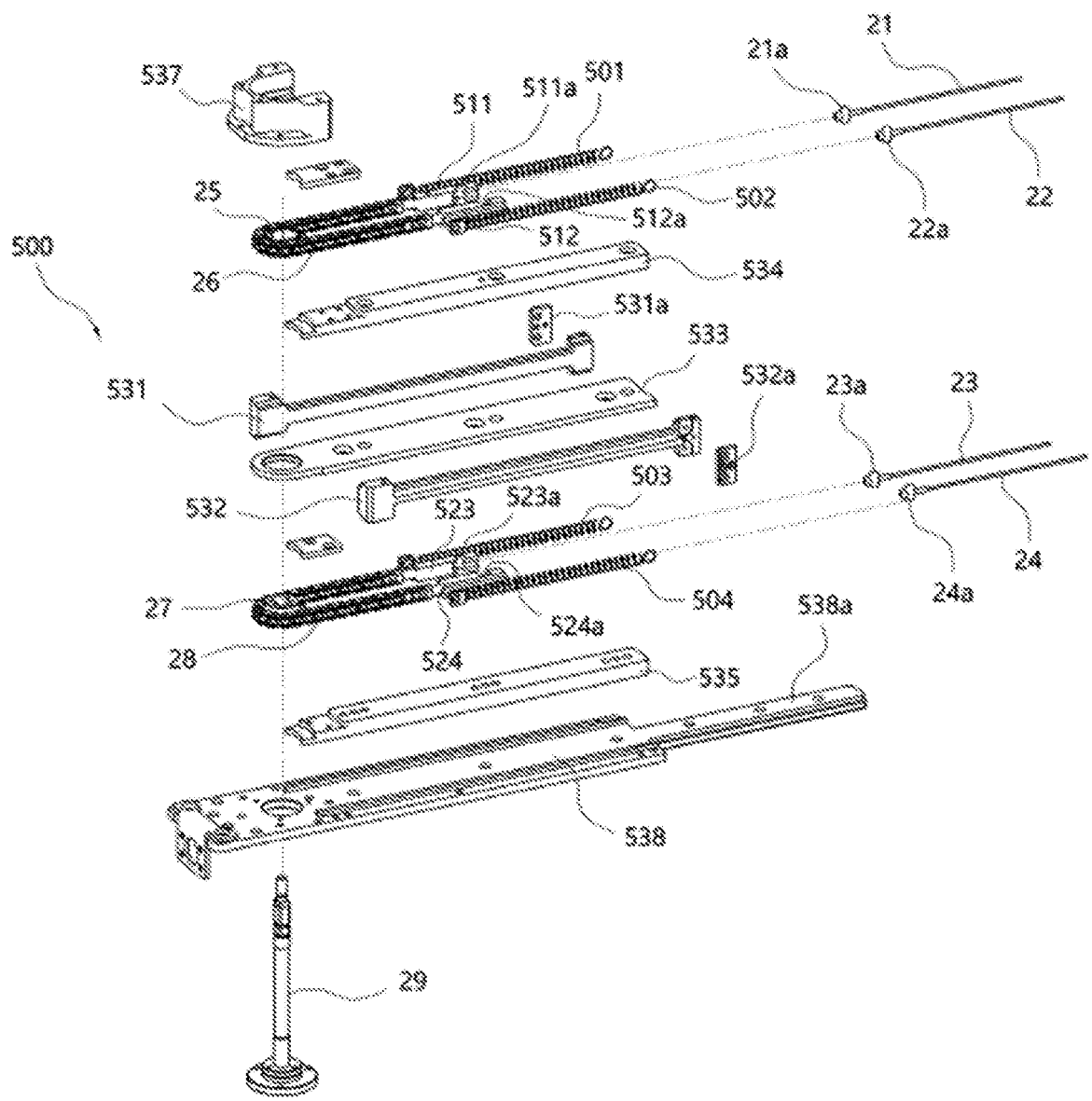
FIG. 4 is a perspective diagram illustrating the overall direction conversion module provided in the endoscope having the chain locking prevention function according to the exemplary embodiment of the present disclosure.
Figure 5:
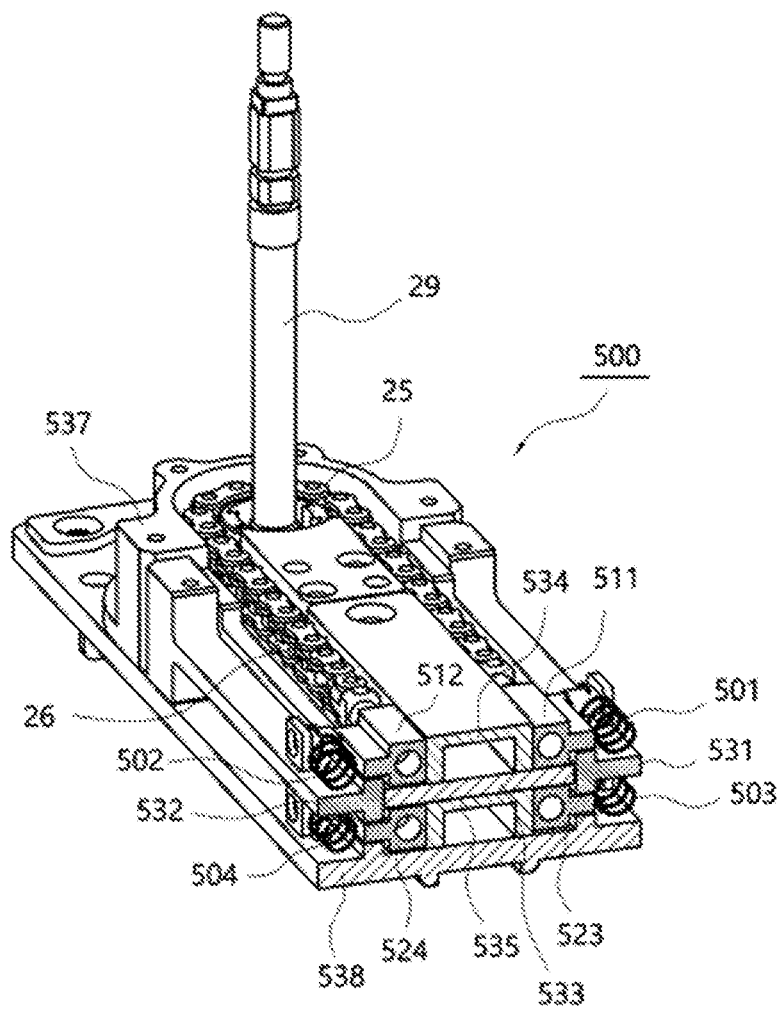
FIG. 5 is a cross-sectional perspective diagram illustrating the direction conversion module provided in the endoscope having the chain locking prevention function according to the exemplary embodiment of the present disclosure.

As illustrated in FIGS. 3, 4, and 5, the direction conversion module 500 includes first and second connection blocks 511, 512 for connecting both ends of the upper chain 26 having the middle portion of the length wound around the upper sprocket 25 and parallel to each other to one end of each of the first and second connection wires 21, 22, and third and fourth connection blocks 523, 524 for connecting both ends of the lower chain 28 having the middle portion of the length wound around the lower sprocket 27 and parallel to each other to one end of each of the third and fourth connection wires 23, 24.

One side surfaces of the first, second, third, and fourth connection blocks 511, 512, 523, 524 have locking grooves 511a, 512a, 523a, 524a recessed to be locked and connected to locking members 21a, 22a, 23a, 24a integrally provided on one end of each of the first, second, third, and fourth connection wires.

The locking groove is provided in the form of a groove opened outward so that the locking member is inserted to be locked and disposed thereto, and a wire placement groove into which the wire is inserted and disposed is recessed on one side surface of each of the first, second, third, and fourth connection blocks 511, 512, 523, 524 in which the locking grooves are formed.

A chain coupling part capable of easily performing the locking-connection and locking-release between the locking member and the locking groove is provided between both ends of each of the upper and lower chains and one end of each of the first, second, third, and fourth connection blocks.

Figure 6:
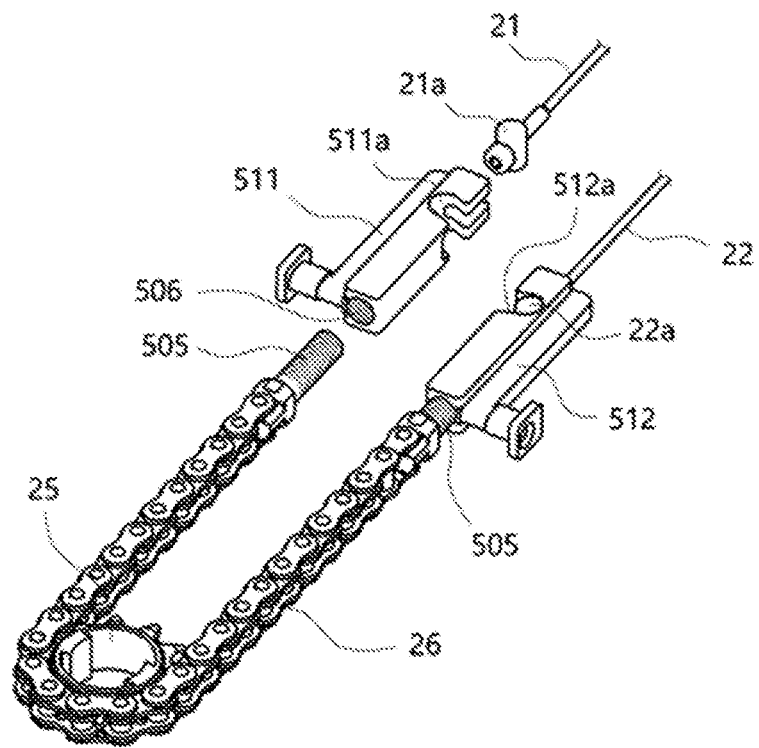
FIG. 6 is a diagram illustrating an adjustment screw part provided to show a connection state between both ends of an upper chain and first and second connection blocks in the direction conversion module provided in the endoscope having the chain locking prevention function according to the exemplary embodiment of the present disclosure.

As illustrated in FIG. 6, the chain coupling part has coupling male screws 505 provided on both ends of the upper chain 26 and rotationally operated, and coupling female screw holes 506 screw-coupled with the coupling male screws on one ends of the first and second connection blocks.

In a state where the locking members 21a, 22a having a substantially T shape are primarily locked and disposed in the respective locking grooves 511a, 512a of the first and second connection blocks, the locking member is secondarily and firmly in close contact with the locking groove to be locked and connected thereto so that the locking member is not separated and detached from the locking groove by pulling the corresponding connection block toward the chain by the locking directional rotation of the coupling male screw 505.

On the other hand, it is possible to easily perform a work of releasing the locking-connection between the connection block and the connection wire and separating them from each other by separating the locking member from the locking groove in a state where the locking member and the locking groove are loosed by forming a gap therebetween by pushing the corresponding connection block toward the insertion part by the unlocking directional rotation of the coupling male screw.

That is, the first, second, third, and fourth connection blocks 511, 512, 523, 524 and the first, second, third, and fourth connection wires 21, 22, 23, 24 may easily perform the locking-connection and locking-release between the locking member and the locking groove by the screw-coupling between the coupling male screw and the coupling female screw hole of the chain coupling part provided between the end of the corresponding connection block and the end of the corresponding chain.

In addition, by disposing a first guide rail 531 having a predetermined length disposed parallel to the upper chain and contacting one side surface of each of the first and third connection blocks vertically located at predetermined intervals in the figure between the first connection block 511 and the third connection block 523, the first guide rail guides the first and third connection blocks to be pulled, and pushed in opposite directions upon selective rotational operation of the upper operation handle.

By disposing a second guide rail 532 having a predetermined length disposed parallel to the lower chain and contacting one side surface of each of the second and fourth connection blocks vertically located at predetermined intervals in the figure between the second connection block 512 and the fourth connection block 524, the second guide rail guides the second and fourth connection blocks to be pulled, and pushed in opposite directions upon selective rotational operation of the lower operation handle.

Here, the direction conversion module 500 includes an intermediate guide plate 533 having both ends contacting the first guide rail 531 and the second guide rail 532, includes an upper guide plate 534 assembled on the upper surface which is one side surface of the intermediate guide plate contacting one side surface of each of the first and second connection blocks 511, 512 and located between both ends of the upper chain 26 parallel to each other, and includes a lower guide plate 535 assembled on the lower surface which is the other side surface of the intermediate guide plate contacting one side surface of each of the third and fourth connection blocks 523, 524 and located between both ends of the lower chain 28 parallel to each other.

Therefore, the intermediate guide plate 533 provided between the first and second guide rails, and the upper and lower guide plates 534, 535 provided on both surfaces of the intermediate guide plate form one guide passage through which the first and second connection blocks and the upper chain are disposed, and guided to be moved in opposite directions, and form the other guide passage through which the third and fourth connection blocks and the lower chain are disposed, and guided to be moved in opposite directions.

In addition, the direction conversion module 500 includes an upper finishing plate 536 assembled above the upper guide plate 534 so that one side surfaces of the first and second connection blocks contact the inner surface thereof while covering the connection portion between the first and second connection blocks 511, 512 and the first and second connection wires, and includes a lower finishing plate 538 assembled below the upper guide plate 535 so that one side surfaces of the third and fourth connection blocks contact the inner surface thereof while covering the connection portion between the third and fourth connection blocks 523, 524 and the third and fourth connection wires 23, 24.

The lower finishing plate 538 has a mount 538a for assembling and connecting with the second detachable module having the first, second, third, and fourth connection wires, the mount 538a extending from one side end thereof by a predetermined length, and has a chain cover 537 for covering the wound portions of the upper and lower chains having the middle portions of the lengths wound around the upper and lower sprockets, the chain cover 537 contacting one ends of the first and second guide rails corresponding to the upper and lower sprockets.

Meanwhile, the direction conversion module 500 includes first and second coil springs 501, 502 having both ends, which are stretched to both sides, connected so as to generate an elastic restoring force between a fixed end, which is one end of each of the first and second guide rails 531, 532 corresponding to the first and second connection wires 21, 22, and the first and second connection blocks 511, 512, respectively.

In this case, by elastically supporting the first and second connection blocks connected to the first and second connection wires toward the insertion part by external forces having predetermined strengths by the elastic restoring forces of the first and second coil springs, it is possible to maintain the linear state of the upper chain wound around the upper sprocket and having both ends connected to the first and second connection blocks, thereby smoothly performing the pulling movement and pushing movement of the upper chain linearly arranged parallel to each other upon selective rotation of the operation part without generating a bending portion.

In addition, the direction conversion module includes the third and fourth coil springs 503, 504 having both ends, which are stretched to both sides, respectively so as to generate elastic restoring forces between a fixed end, which is one end of each of the first and second guide rails 531, 532 corresponding to the third and fourth connection wires 23, 24, and the third and fourth connection blocks 523, 524.

In this case, as in the foregoing, by elastically supporting the third and fourth connection blocks connected to the third and fourth connection wires toward the insertion part by external forces having predetermined strengths by the elastic forces of the third and fourth coil springs, it is possible to maintain the linear state of the lower chain wound around the lower sprocket and having both ends connected to the third and fourth connection blocks, thereby smoothly performing the pulling movement and pushing movement of the lower chain linearly arranged parallel to each other upon selective rotation of the operation part without generating a bending portion.

At this time, the fixed ends, which are one ends of the first and second guide rails 531, 532, include a locking pin by which one end of each of the first, second, third, and fourth coil springs 501, 502, 503, 504 is locked and fixed, and the first and second guide rails 531, 532 include pin fixing plates 531a, 532a assembled to the fixed ends which are one ends of the first and second guide rails to fixedly locate the locking pins.

In addition, the first and second coil springs 501, 502 have both sides connected between the first and second connection blocks and the first and second guide rails in a state of being stretched at the same lengths as each other so as to transfer the external forces having the same strengths to both ends of the upper chain through the first and second connection blocks 511, 512 to maintain the linear state of the upper chain, thereby generating the same elastic restoring forces as each other.

Likewise, the third and fourth coil springs 503, 504 have both sides connected between the third and fourth connection blocks and the first and second guide rails in a state of being stretched at the same lengths as each other so as to transfer the external forces having the same strengths to both ends of the lower chain through the third and fourth connection blocks 523, 524 to maintain the linear state of the lower chain, thereby generating the same elastic restoring forces as each other.

In addition, both ends of each of the first and second coil springs 501, 502 and both ends of each of the third and fourth coil springs 503, 504 may be locked and connected in the state of being stretched to both sides at the lengths having the same sizes so as to transfer the external forces having the same strengths to the upper and lower chains but are not limited thereto and may be locked and connected in a state of being stretched at the lengths having different sizes.

Therefore, the upper chain wound around the upper sprocket and arranged parallel to each other may be elastically supported by the insertion part side together with the first and second connection blocks by the external forces having predetermined strengths at all times by the elastic restoring forces of the first and second coil springs having both ends locked and connected between the first and second connection blocks and the first and second guide rails, thereby stably maintaining the parallel state of the upper chain arranged parallel to each other and linearly moving in opposite directions.

In addition, the lower chain wound around the lower sprocket and arranged parallel to each other may be elastically supported by the insertion part side together with the third and fourth connection blocks by the external forces having predetermined strengths at all times by the elastic restoring forces of the third and fourth coil springs having both ends locked and connected between the third and fourth connection blocks and the first and second guide rails, thereby stably maintaining the parallel state of the lower chain arranged parallel to each other and linearly moving in opposite directions.

The direction conversion module 500 having the above configuration pulls and moves, and pushes and moves both ends of any one of the upper and lower chains wound around the sprockets in opposite directions while rotating any one of the upper and lower sprockets by the rotation of any one of the selective upper and lower operation handles of the operation part.

By pulling and pushing the wire in conjunction with the selective linear movements of the upper and lower chains, the endoscopic surgery is performed while operating the front end of the insertion part inserted into the body to be bent vertically and horizontally.

Figure 7A:
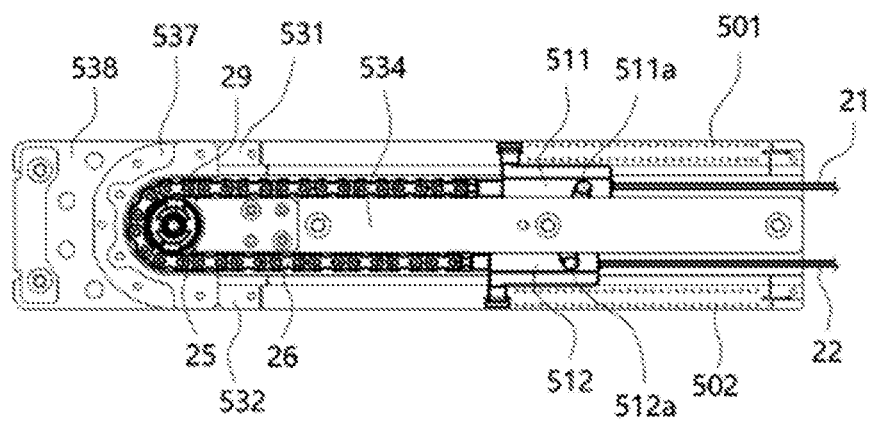
FIGS. 7A, 7B, and 7C are diagrams illustrating operation states of the direction conversion module provided in the endoscope having the chain locking prevention function according to the exemplary embodiment of the present disclosure.

As illustrated in FIG. 7A, the first and second connection blocks 511, 512 of the direction conversion module 500 are elastically supported by the insertion part side, which is the right in the figure, by the external force caused by the elastic restoring forces of the first and second coil springs 501, 502 connected in the state of being stretched to both sides between the first and second connection blocks 511, 512 and the fixed ends, which are one ends of the first and second guide rails.

Here, the rest of the upper chains 26 having the middle portion of the length wound around the upper sprocket 25 stands by to be arranged parallel to each other at the same lengths as each other, thereby maintaining the state of being parallel to each other and linear, and the first and second connection blocks 511, 512 stand by at the same location as each other.

Figure 7B:
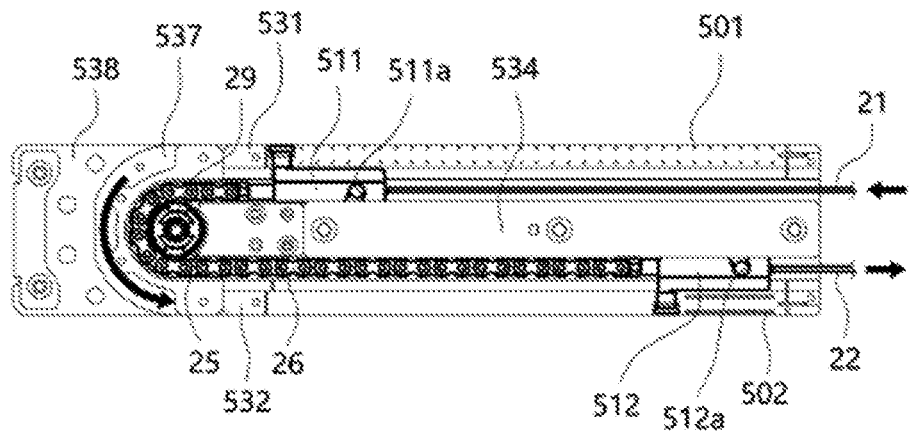

In this initial standby state, as illustrated in FIG. 7B, when the upper sprocket of the rotary shaft is rotated in one direction, that is, counterclockwise in the figure by the selective rotational operation of the operation part, the first connection block 511 is pulled toward the operation part together with the first connection wire connected to the first connection block by a predetermined distance, whereas the second connection block 512 is pushed toward the insertion part together with the second connection wire connected to the second connection block by a predetermined distance corresponding to the pulling movement distance of the first connection block.

At this time, the entire length of the first coil spring 501 having both ends connected between the first connection block 511 and the first guide rail 531 is increased to both sides by the pulling movement distance to increase the elastic restoring force compared to the initial standby state, whereas the entire length of the second coil spring 502 having both ends connected between the second connection block 512 and the second guide rail 532 is relatively decreased by the pushing movement distance to decrease the elastic restoring force compared to the initial standby state.

In this case, the elastic restoring forces generated in the first and second coil springs are different from each other, but it is possible to maintain the state where the external force caused by the elastic restoring force is transferred to the upper chain wound around the upper sprocket and pushed toward the insertion part, thereby stably maintaining the linear state of the upper chain which is pushed to lengthily extend.

Figure 7C:
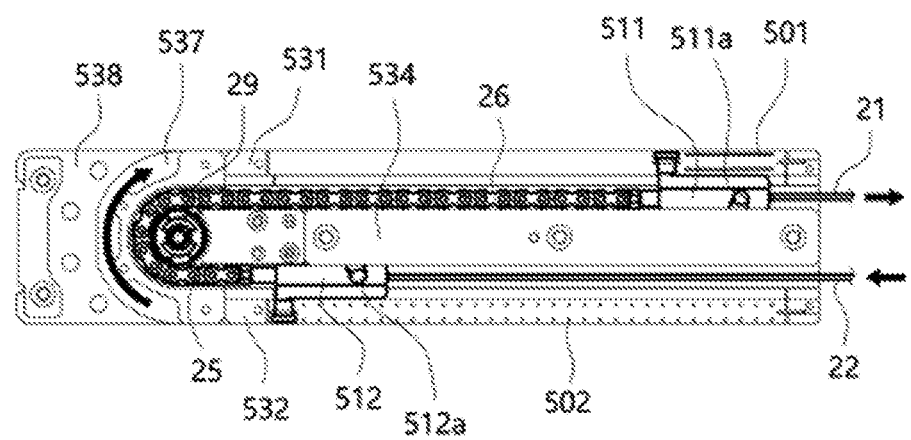
Figure 8:
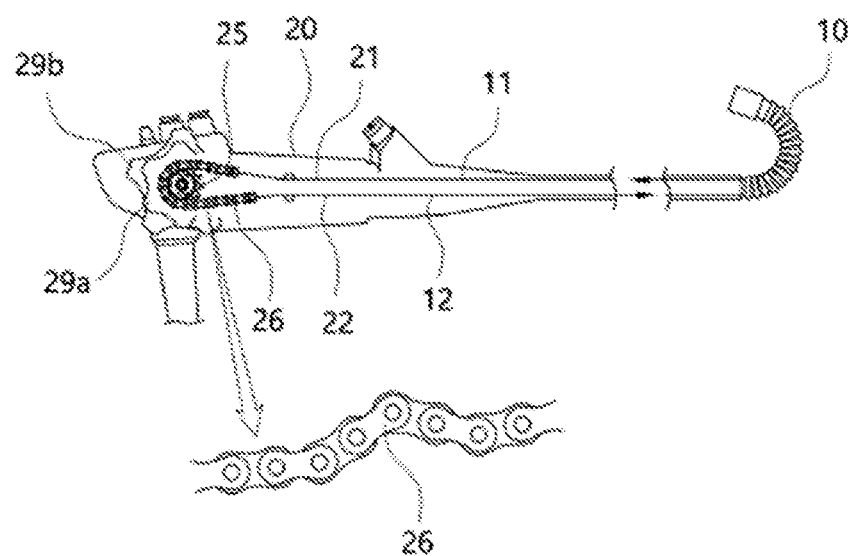
FIG. 8 is a schematic diagram illustrating a general endoscope.

In addition, contrary to the above, as illustrated in FIG. 7C, when the upper sprocket of the rotary shaft is rotated reversely, that is, clockwise in the figure by the selective rotational operation of the operation part, the second connection block 512 is pulled toward the operation part together with the second connection wire connected to the second connection block by a predetermined distance, whereas the first connection block 511 is pushed toward the insertion part together with the first connection wire connected to the first connection block by a predetermined distance corresponding to the pulling movement distance of the second connection block.

At this time, the entire length of the second coil spring 502 having both ends connected between the second connection block 512 and the second guide rail 532 is increased to both sides by the pulling movement distance to increase the elastic restoring force compared to the initial standby state, whereas the entire length of the first coil spring 501 having both ends connected between the first connection block 511 and the first guide rail 521 is decreased by the pushing movement distance to decrease the elastic restoring force compared to the initial standby state.

In this case, the elastic restoring forces generated in the first and second coil springs are different from each other as in the foregoing, but it is possible to maintain the state where the external force caused by the elastic restoring force is transferred to the lower chain wound around the lower sprocket and pushed toward the insertion part, thereby stably maintaining the linear state of the lower chain which is pushed to lengthily extend.

Therefore, the external forces caused by the elastic restoring forces of the first and second coil springs may be transferred to the upper chain pulled, and pushed in opposite directions upon selective rotational operation of the operation part to maintain the linear state of the upper chain, thereby preventing the narrowness with other members or the occurrence of noise due to the unnecessary bending of the link connection portion of the chain and smoothly performing the pulling movement and the pushing movement of the upper chain.

Meanwhile, maintaining the lower chain parallel to each other in the linear state by applying the external forces caused by the elastic restoring forces of the third and fourth coil springs to the lower chain while the lower chain wound around the lower sprocket is pulled, and pushed in opposite directions by the lower operation handle of the operation part is the same as in the upper chain, so that the detailed description thereof will be omitted.

The aforementioned present disclosure is not limited to the aforementioned exemplary embodiments and the accompanying drawings, and it will be apparent to those skilled in the art to which the present disclosure pertains that various substitutions, modifications, and changes are possible without departing from the technical spirit of the present disclosure.

The invention claimed is:

1. An endoscope having chain locking prevention function, the endoscope comprising:
   an insertion part having a lighting photographing part on a front end thereof;
   an operation part having an upper chain and a lower chain wound around an upper sprocket and a lower sprocket of a rotary shaft for operating the front end of the insertion part to be bent; and
   a direction conversion module for converting rotational motions of the upper sprocket and the lower sprocket to linear motions of the upper chain and the lower chain, wherein the direction conversion module comprises:
   a lower finishing plate;
   a first connection block and a second connection block for connecting both ends of the upper chain to a first connection wire and a second connection wire of the operation part;
   a third connection block and a fourth connection block for connecting both ends of the lower chain to a third connection wire and a fourth connection wire of the operation part;
   a first guide rail having a predetermined length and disposed between the first connection block and the third connection block to guide slide movements of the first connection block and the third connection block, wherein the first guide rail is fixed to the lower finishing plate;
   a second guide rail having a predetermined length and disposed between the second connection block and the fourth connection block to guide slide movements of the second connection block and the fourth connection block, wherein the second guide rail is fixed to the lower finishing plate;
   a chain cover having a rounded surface for covering wound portions of the upper chain and the lower chain, wherein the chain cover is fixed to the lower finishing plate;
   a first coil spring and a second coil spring elastically supporting the first connection block and the second connection block connected to the first connection wire and the second connection wire toward the insertion part to maintain a linear state of the upper chain, wherein the first coil spring and the second coil spring are configured to be stretched to generate elastic restoring forces, so as to transfer external forces to both ends of the upper chain through the first connection block and the second connection block, wherein the first coil spring has a proximal end directly connected to the first connection block and a distal end directly connected to a fixed end of the first guide rail, and wherein the second coil spring has a proximal end directly connected to the second connection block and a distal end directly connected to a fixed end of a second guide rail; and
   a third coil spring and a fourth coil spring elastically supporting the third connection block and the fourth connection block connected to the third connection wire and the fourth connection wire toward the insertion part to maintain a linear state of the lower chain, wherein the third coil spring and the fourth coil spring are configured to be stretched to generate elastic restoring forces, so as to transfer external forces to both ends of the lower chain through the third connection block and the fourth connection block, wherein the third coil spring has a proximal end directly connected to the third connection block and a distal end directly connected to the fixed end of the first guide rail, and wherein the fourth coil spring has a proximal end directly connected to the fourth connection block and a distal end directly connected to the fixed end of the second guide rail.

2. The endoscope having the chain locking prevention function of claim 1,
wherein the direction conversion module further comprises:
an intermediate guide plate disposed between the first guide rail and the second guide rail;
an upper guide plate disposed on a top surface of the intermediate guide plate and contacting the first connection block and the second connection block; and
a lower guide plate disposed on a bottom surface of the intermediate guide plate and contacting the third connection block and the fourth connection block.

3. The endoscope having the chain locking prevention function of claim 2,
wherein the direction conversion module further comprises:
an upper finishing plate disposed above the upper guide plate for guiding a first connection portion between the first connection block and the first connection wire and a second connection portion between the second connection block and the second connection wire,
wherein the lower finishing plate is disposed under the lower guide plate for guiding a third connection portion between the third connection block and the third connection wire and a fourth connection portion between the fourth connection block and the fourth connection wire.

* * * * *